United States Patent [19]

Binder

[11] Patent Number: 5,670,484

[45] Date of Patent: Sep. 23, 1997

[54] METHOD FOR TREATMENT OF SKIN LESIONS ASSOCIATED WITH CUTANEOUS CELL-PROLIFERATIVE DISORDERS

[76] Inventor: William J. Binder, 1640 Amalfi Dr., Pacific Palisades, Calif. 90272

[21] Appl. No.: 372,054

[22] Filed: Jan. 12, 1995

Related U.S. Application Data

[63] Continuation-in-part of Ser. No. 240,973, May 9, 1994, abandoned.

[51] Int. Cl.$^6$ .......................... A61K 38/10; A61K 38/04
[52] U.S. Cl. ................................................. 514/14; 514/2
[58] Field of Search ................................................ 514/14, 2

[56] References Cited

FOREIGN PATENT DOCUMENTS

WO9305800  4/1993  WIPO .

OTHER PUBLICATIONS

Physicans' Desk Reference, pp. 792–797, 1994.

Olosen, *Clinical and pathophysiological observations in migraine and tension–type headache explained by integration of vascular, supraspinal and myofascial inputs*, pp. 125–129, Pain, vol. 46, 1991.

Blitzer et al., Abstract Title, *The management of hyperfunctional facial lines with botulinum toxin: a collaborative study of 200 patients*, 1992.

Borodic, et al., *Botulinum A toxin for treatment of aberrant facial nerve regeneration*, P & R Surgery, May 1993, vol. 91, No. 6, pp. 1042–1045.

Borodic, et al., *Botulinum A toxin for the treatment of adult–onset spasmodic torticollis*, P & R Surgery, Feb. 1991, vol. 87, No. 2, pp. 285–289.

Jankovic, et al., *Therapeutic uses of botulinum toxin*, New England Journal of Medicine, Apr. 25, 1991, 324:1186–1194.

Keen, et al., *Botulinum toxin for hyperkinetic facial lines: results of a double blind placebo controlled study*, Jan. 15, 1993, presented in part at the winter meeting of the American Academy of Facial Plastic and Reconstructive Surgery, Boca Raton, Fla.

Anderson et al., *Medline Abstracts*, abstract #93059130, 1992.

Jedynak et al., *Biological Abstracts*, vol. 90, No. 7, abstract #79336, 1990.

Yakoleff et al., *Biological Abstracts*, vol. 97, No. 3, abstract #33434, 1993.

*Primary Examiner*—William R. A. Jarvis
*Attorney, Agent, or Firm*—Chadbourne & Parke LLP

[57] ABSTRACT

The invention is a method for treatment of cutaneous cell-proliferative disorders. More specifically, the method of the invention is useful in mitigating and inducing remission of lesions associated with such disorders and in controlling related symptoms of the disorders (such as scaling and itching). According to the method of the invention, an invertebrate neurotoxin is administered to the skin of the host at or near the site of a lesion. The preferred neurotoxin for use in the method of the invention is Botulinum toxin, particularly Botulinum toxin A.

9 Claims, No Drawings

METHOD FOR TREATMENT OF SKIN LESIONS ASSOCIATED WITH CUTANEOUS CELL-PROLIFERATIVE DISORDERS

RELATED PATENT APPLICATIONS

This is a continuation-in-part of U.S. patent application Ser. No. 08/240,973, filed May 9, 1994, now abandoned.

BACKGROUND OF THE INVENTION

1. Field of the Invention

The invention relates to the pharmacological treatment of skin lesions manifested in a host suffering from a cutaneous cell-proliferative disorder, particularly psoriasis and dermatitis. More specifically, the invention relates to the treatment of such skin lesions by administering a therapeutically effective dosage of pharmaceutically safe neurotoxin, in particular Botulinum toxin A, to the host.

2. History of the Prior Art

Psoriasis is a skin disorder which is believed to affect approximately 1.5% to 2% of the U.S. population with varying degrees of severity. Of this group, about 5% to 8% will also develop psoriatic arthritis, typically in peripheral joints.

Psoriasis is manifested by the development of lesions consisting of red patches of skin covered with whitish, pruritic scales. The lesions derive from a discrete increase in the normal number of basal cells of the epidermis. The cell population at the site of a lesion can turn over in about 3–4 days, compared to 27 days or more for normal skin. Psoriatic lesions may be comprised of elevated papules (papulosquamous lesions), reddish erosions (erythroderma) and/or pustules. Whatever their form, the lesions tend to be sharply demarcated, but can migrate from one location to another in the host skin. Typically, the lesions are formed on the skin of the arms, legs, elbows, knees, scalp or genitals where they may remain for periods of several weeks to several months.

Although psoriasis is believed to have a genetic component, both its cause and cure are unknown. Thus, present treatments for psoriasis are directed toward controlling, rather than eliminating, the abnormally rapid proliferation of the epidermis which characterizes the disease. Since 1974, the most common method of treatment has been PUVA (psoralan ultraviolet A), wherein psoralan is given to sensitize the skin to ultraviolet light before the skin is exposed to ultraviolet light (A waves) for discrete periods of time to slow the production of new skin cells in affected areas.

In addition, 1,25-dihydroxyvitamin $D_3$ and nonhypercalcemic analogs thereof have recently been approved for use in topical preparations by the United States Food and Drug Administration for the treatment of psoriasis. Corticosteriods may also be given to address the itching and discomfort associated with psoriatic lesions.

Lesions similar to those which appear in the skin of patients suffering from psoriasis also appear in the skin of patients suffering from certain forms of dermatitis (eczema), including atopic and seborrheic dermatitis, as well as other less common cutaneous disorders, such as pityriasis rubra pilaris, pityriasis rosea and lichen simplex. Again, the cause of these non-contact dermatoses are largely unknown, although allergies and stress are believed to be related to the onset of lesion formation in many individuals. Corticosteriods and topical agents such as coal tar based ointments and shampoos are frequently applied to control the growth and spread of lesions.

The scaling and irritation which accompanies the formation of benign cutaneous lesions can also occur on formation of malignant lesions. Topical corticosteroids and emollients, though not curative of such lesions, can provide a measure of temporary relief of symptoms associated with the lesions for the patient.

Although topical use of vitamin $D_3$ is a promising new therapy for psoriasis, the range of treatment available for psoriasis and the symptoms of other cell-proliferative disorders of the skin is narrow and largely palliative in nature. A drawback shared by each available treatment is the need for frequent repetition, particularly of applications of topical corticosteroids. Cessation or interruption of treatment will often result in reappearance and even exacerbation of the patient's condition.

A need, therefore, exists for a treatment for skin lesions associated with cutaneous cell-proliferative disorders which is both effective and relatively long-lasting. To that end, the present invention provides a method for treating such skin lesions through administration to the skin (including the epidermal, dermal, subdermal and subcutaneous layers thereof) of a neurotoxin, in particular, Botulinum A.

Administration by injection of neurotoxins (such as invertebrate exotoxins) into or near muscle tissue has gained acceptance as a therapeutic modality for certain neuromuscular disorders. For example, serotype A of the Botulinum toxin (produced by *Clostridium botulinum*) has been recommended in the art for use for the treatment of certain diseases such as disorders of the extraocular muscles (e.g., comitant strabismus and nystagmus) as well as dystonias (involuntary contractions of facial muscle) (see. e.g., *The New England Journal of Medicine*, 324: 1186–1194, 1991). In this context, Botulinum toxin A is believed to produce a reversible, flaccid paralysis of mammalian skeletal muscle, presumably by blocking the exocytosis of acetylcholine at peripheral, presynaptic cholinergic receptors, with limited activity at receptors in the central nervous system (Rabasseda, et al., *Toxicon*, 26:329–326, 1988). Botulinum toxin A is not believed to result in degeneration of nervous or muscular tissue and has been approved for use in certain therapies by the U.S. Food and Drug Administration.

Other serotypes of the Botulinum toxin have been identified that have immunologically distinct phenotypes; i.e., serotypes B, C1, C2, D, F and G (Simpson, et al., *Pharmacol.Rev.*, 33:155–188, 1981). All of the serotypes are believed to be proteins of about 150 kDa molecular weight that are comprised of two polypeptide chains linked by disulphide bridges. The shorter of the two chains is believed to be responsible for the toxicity of the toxin, while the longer of the two chains is believed to be responsible for the penetration of the toxin into nervous tissue. Although antigenically different to some extent, the Botulinum serotypes are believed to be similar in their pharmacological actions (Brin, et al., "Report of the Therapeutics and Technology Assessment Subcommittee of the American Academy of Neurology", *Neurology*, 40:1332–1336, 1990).

In addition, like serotype A, serotypes B and E of the Botulinum toxin have been linked to cases of botulism in humans. Thus, having the same pathological activity as serotype A, serotypes B and E can be reasonably expected to have essentially the same biological activity as serotype A. Other invertebrate toxins are known, or can reasonably be expected, to share the mode of action of Botulinum toxin. For example, serotypes A and E of the Botulinum toxin share a substantial degree of sequence homology with the Tetanus neurotoxin produced by *Clostridium tetani* (DasGupta, et al., *Biochemie*, 71:1193–1200, 1989). Further, although the tetanus neurotoxin typically acts on the central nervous system to produce rigid rather than flaccid muscle paralysis, at least one peptide digestion fragment of the tetanus toxin (fragment Ibc, which is produced as a papain cleavage product) have been shown to act peripherally to produce flaccid paralysis in a manner similar to botulinum toxin (Fedinic, et al., *Boll. 1st. Sieroter Milan*, 64:35–41, 1985;and, Gawade, et al., *Brain Res.*, 334:139–46, 1985).

Reversible, flaccid paralysis has also been observed following intrathecal injection of acylpolyamine toxins, anticholinergic, presynaptic neurotoxins that are produced in the venom of many invertebrates (Herold, et al., *Anesthesiology*, 77:507–512, 1992). In particular, two toxins (AR636 and AG489) from spiders *Argiope aurantia* and *Agelenopsis aperta* have been shown to produce motor inhibition at a dosage of 2 micrograms while 7 micrograms was an effective dosage to produce sensory inhibition.

Despite the apparent effects of such neurotoxins on motor and sensory activity in mammals, the use of such toxins in humans to date has been limited. In particular, such toxins have neither been used nor suggested for use to treat skin disorders such as psoriasis and dermatitis.

SUMMARY OF THE INVENTION

The invention provides a method for treating cutaneous cell-proliferative disorders. Specifically, the invention comprises administering a therapeutically effective amount of a pharmaceutically safe invertebrate presynaptic neurotoxin (hereafter, "neurotoxin") to a host in need of such treatment. The neurotoxin will preferably be administered subdermally or subcutaneously, but may also be administered by topical and transdermal routes of administration.

The preferred neurotoxin of the invention is Botulinum toxin A. Neurotoxins which are equivalent in pharmacology to Botulinum A are also suitable for use in the method of the invention.

A particular advantage of the method of the invention is the relatively prolonged mitigation or remission of lesions in the treated area which may be achieved. For example, while relapse following cessation of corticosteroid or PUVA treatment may occur within a matter of days, affected areas treated according to the method of the invention may become and remain lesion free at the site of treatment for periods of several months.

DETAILED DESCRIPTION OF THE PREFERRED EMBODIMENTS

A. PRESYNAPTIC NEUROTOXIN COMPOSITIONS FOR USE IN THE METHOD OF THE INVENTION

The target tissue for administration of neurotoxin according to the invention is skin. "Skin" as used in this disclosure shall refer to the tissue comprised of epidermal, dermal, subdermal and subcutaneous layers of cells.

"Neurotoxin" as used in this disclosure refers to both invertebrate toxins and biologically active peptide fragments of proteinaceous invertebrate toxins. The neurotoxins of the invention will be those neurotoxins that exert a biological effect in mammals which is equivalent to the effect exerted by Botulinum toxin, particularly Botulinum toxin A.

In this respect, Botulinum toxin is known to produce reversible, flaccid paralysis of musculature in mammals on intramuscular injection but does not result in degeneration of muscle or nervous tissue. It is believed that this effect is the result of inhibition by Botulinum toxin of the release of acetylcholine from presynaptic vesicles of nerve endings. Other neurotoxins (e.g., Botulinum serotypes B and E) can be reasonably assumed to have similar modes of action to produce physiologically equivalent physiological responses.

The modality by which Botulinum toxin A achieves the effects described herein is unknown, but may be independent of its known activity (as an anticholinergic agent). However, it can be reasonably predicted that neurotoxins which possess biological activity similar to the known activity of Botulinum toxin A will also share in the latter's ability to reduce the number, severity and/or frequency of appearance of lesions on the skin of patients suffering from primary cutaneous disorders such as psoriasis and dermatitis (i.e., the "biological activity of the invention").

The preferred neurotoxin of the invention is Botulinum toxin. Serotype A of this toxin is commercially available and is presently supplied by Allergan, Inc. of Irvine, Calif. under the tradename "BOTOX and by Porton Products Ltd, of the United Kingdom under the tradename "DYSPORT". A pentavalent toxoid of all eight known Botulinum serotypes is also available as an investigational drug from the U.S. Center for Disease Control in Atlanta, Ga. Of these, the Botulinum A toxin preparations are most preferred for their known safety and efficacy.

Tetanus toxins for use as vaccines are also commercially available (from, for example, Lederle Laboratories of Wayne, N.J. under the tradename "TETANUS TOXOID PUROGENATED"). As discussed above, the Ibc fragment of the Tetanus toxin is believed to act peripherally and is therefore likely to be similar in its activity to Botulinum toxin. Therefore, the method of the invention will preferably encompass the use of pharmaceutically safe forms of the Ibc fragment of the Tetanus toxin rather than the use of intact Tetanus toxin.

Those of ordinary skill in the art will know, or can readily ascertain, how to obtain the neurotoxins of the invention, including the Botulinum and Tetanus toxins, in a pharmaceutically safe form; preferably, a form that is nonteratogenic and does not induce a detectable immune response to the toxin antigen. For most of the neurotoxins of the invention, pharmaceutical safety will be dose-dependent such that relatively low dosages of toxin will be "safe" as compared to dosages which are known to be sufficient to produce disease.

Preferably, the neurotoxins of the invention will be administered as a composition in a pharmaceutically acceptable carrier. To that end, presynaptic neurotoxin compositions are prepared for administration by mixing a toxin the desired degree of purity with physiologically acceptable sterile carriers. Such carriers will be nontoxic to recipients at the dosages and concentrations employed. Ordinarily, the preparation of such compositions entails combining the neurotoxin with buffers, antioxidants such as ascorbic acid, low molecular weight (less than about 10 residues) polypeptides, proteins, amino acids, carbohydrates including glucose or dextrins, chelating agents such as EDTA, glutathione and other stabilizers and excipients. Such compositions may also be lyophilized and will be pharmaceutically acceptable; i.e., suitably prepared and approved for use in the desired application.

For transdermal and topical administration, the neurotoxin will preferably be formulated to enhance penetration of the neurotoxin to and across the stratum corneum of the skin. Those of ordinary skill in the art will be familiar with, or can readily ascertain the identity of, excipients and additives which will facilitate drug delivery (particularly of peptides) across skin. For review in this respect, reference may be made to *"Novel Drug Delivery Systems"*, Chien, ed. (Marcel Dekker, 1992), the disclosure of which is incorporated herein by this reference to illustrate the state of knowledge in the art concerning drug delivery to and across the stratum corneum of skin.

Most preferably, the neurotoxin will be formulated in unit dosage form for ease of administration. For example, the neurotoxin may be supplied as a sterile solution or lyophilized powder in a vial.

B. METHODS FOR ADMINISTRATION OF THE NEUROTOXINS OF THE INVENTION

Generally, the dose of presynaptic neurotoxin to be administered will vary with the age, presenting condition and weight of the host to be treated. Suitable candidates for treatment according to the method of the invention will be persons suffering from cutaneous cell-proliferative disorders; i.e., disorders of the skin which include as symptoms the development of lesions. In this respect, "lesions" shall mean a population of cells which has undergone, or is predisposed to undergo, an abnormally high rate of cellular growth. Predisposition to such growth may be determined according to conventional clinical standards, such as a prior or contemporaneous diagnosis or family history of a cutaneous cell-proliferative disorder (e.g, psoriasis, dermatitis, and forms of pityriasis, such as pitiyriasis rosea, pityriasis rosacea and pityriasis rubra).

The potency of the neurotoxin will also be considered. Toxin potency is expressed as a multiple of the $LD_{50}$ value for a reference mammal, usually a mouse. Where a mouse is the reference mammal, one "unit" of toxin is the amount of toxin that kills 50% of a group of mice that were disease-free prior to inoculation with the toxin. For example, commercially available Botulinum toxin A typically has a potency such that one nanogram contains about 40 mouse units. The potency in humans of the Botulinum toxin A product supplied by Allergan, Inc. under the registered trademark "BOTOX" is believed to be about $LD_{50}$=2,730 units.

Assuming a potency which is substantially equivalent to $LD_{50}$=2,730 units, the neurotoxin can be administered in a dose of up to about 1000 units, although individual dosages of about 5–15 units are preferred while dosages of as low as about 2 to 5 units will have therapeutic efficacy and are particularly preferred for initial treatments and treatments where the neurotoxin is applied to more than one lesion or area at a time. The dosage may also be adjusted upward or downward depending on the size of each lesion to be treated. Generally, the neurotoxin will be administered as a composition at a dosage that is proportionally equivalent to about 2.5 cc/100 units. Those of ordinary skill in the art will know, or can readily ascertain, how to adjust these dosages for neurotoxins of greater or lesser potency.

Preferably, the lowest therapeutically effective dosage (i.e., the dosage which results in detection by the patient of a reduction in the occurrence, number and/or severity of skin lesions and associated discomfort experienced by the patient) will be administered. In the initial treatment, a low dosage may be administered at one site to determine the patient's sensitivity to, and tolerance of, the neurotoxin. Additional injections of the same or different dosages will be administered as necessary.

In this respect, although the mechanism of action by which the method of the invention achieves therapeutic benefits is unknown, it is possible that the neurotoxin administered according to the invention causes a slowing of the growth cycle of cells at the affected site. If this prediction is accurate, then the relative efficacy of treatment may depend on whether the cells to be treated are in a phase of growth which is most susceptible to modulation; i.e., during DNA synthesis. Thus, the efficacy of the method of treatment of the invention will likely be enhanced by repeating the treatment at a later time when the cells to be treated are likely to be undergoing a different phase of growth. The need for such repetition can be determined by gauging whether the treated lesions have reduced in size, improved in appearance, or gone into remission within about 7 to 10 days after treatment.

For many indications, subcutaneous or subdermal injection at the site of a lesion or at a region of skin affected by lesions will be the most efficacious route of administration. Preferably, the injection will be provided to the subcutaneous or subdermal region beneath the lesion by inserting the needle under the lesion from its side. However, where the lesion is too large or otherwise not susceptible to this approach, the injection can be provided through the lesion to the underlying layers of skin. Alternatively, the neurotoxin may be administered by transdermal or topical routes at the site of one or more lesions. However, it is expected that these latter routes will be less efficacious than subcutaneous or subdermal injection and may, therefore, be best used for subacute manifestations.

The injections will be repeated as necessary. As a general guideline, it has been observed that, after administration of Botulinum toxin A into or near lesions in adult human skin according to the method of the invention, the treated site has remained lesion free for periods of at least 2 months. However, Botulinum A toxin in particular is expected to be most effective when administered according to the method of the invention soon after the appearance of any new lesions. Depending on the course of therapy applied (i.e., with respect to dosage, frequency of treatment and sensitivity of individual patients to treatment), the method of the invention can be expected to be effective in mitigating lesions (e.g., by reducing their size or incidence), inducing remission of the disorder (e.g., by eliminating existing lesions), and in controlling symptoms associated with the disorder (e.g., scaling of lesions and itching).

The invention having been fully described, examples illustrating its practice are set forth below. These examples should not, however, be considered to limit the scope of the invention, which is defined by the appended claims.

In the examples, the abbreviation "min" refers to minutes, "hrs" and "h" refer to hours, "mo" and "mos" refers to months, "yr" and "yrs" refer to years, and measurement units (such as "ml") are referred to by standard abbreviations. "Cm." refers to the diameter of each lesion described. "Remission" refers to the complete disappearance of a lesion, while "mitigation" refers to a reduction in the size of a lesion. "F" refers to female and "M" refers to male. All dosages were of BOTOX® and were administered by subcutaneous injection unless otherwise indicated.

EXAMPLE I

Administration of Bitulinum Toxin A to Treat Skin Lesions Associated with Cutaneous Cell-Proliferative Disorders 7 adult, human patients received subcutaneous and/or subdermal injections of Botulinum toxin A ("BOTOX®"), reconstituted with saline to a concentration of 2.5 cc/100 units. The toxin was administered at sites where at least one lesion was present on the patient's skin.

Additional details of the case history, treatment, and post-treatment history of patients within the headache group who agreed to the provide such information are tabulated below in Table 1.

TABLE 1

| Age/Sex | Presenting Condition | Prior Treatment | Site of Lesion(s)/ Delivery | Dosage and Frequency of Injection | Post Injection Condition |
|---|---|---|---|---|---|
| 34/M | Chronic psoriasis. Lesions typically appear and heal in about a 45 day cycle. | Topical and systemic corticosteroids; PUVA. | 2.5 cm. lesion, right leg. | 2 units on 8/26/94. | Lesion in remission by 9/1/94. Had not returned by 12/94. |
| 58/M | Dermatitis (severe eczema) as a child. Chronic psoriasis as an adult. | Topical and systemic corticosteroids; sunlight, bleach, abrasion of lesions. | Right elbow (2 lesions @ 2–3 cm.); left elbow (2 lesions @ 2–4 cm.); right ankle (1 lesion @ 10–12 cm.) | Right elbow: 5 units. Left elbow: 3 units. Right ankle: 5 units Administered in 10/94. | Right elbow: lesion in remission within about 1 week. Left elbow: mitigated to nearly 100% in same period. Right ankle: mitigated to nearly 100% in one week. No return of lesions at right elbow by 12/94; lesions at other sites had not increased in size or severity by 12/94. |
| 62/F | Severe eczema from childhood | Topical emollients and corticosteroids. | 3 lesions on the left arm (@ 2–5 cm.) | 5 units at site of one 2 cm. lesion on 10/5/94. | Treated lesion in remission within 6 days. Some mitigation observed of untreated lesions. By 12/94, treated lesion had not returned and no new lesions had developed in the surrounding area. |
| 42/M | Seborrheic dermatitis and psoriasis (latter for 10 years) | Topical and systemic corticosteroids. | Scalp: one 1.5 cm. lesion. | 5 units at site of lesion on 11/7/94. | Lesion in remission within 5 days. Had not returned by 12/94. |
| 31/M | Seborrheic dermatitis and psoriasis. | Salicylic acid, fluoanoline cream; topical clobetasol propionate. | Scalp: one 3 cm. lesion. Postauricular area (ear): one 2 cm. lesion. | 10 units at site of scalp lesion. 7 units at site of postauricular lesion. Both injections on 10/31/94. | Scalp lesion mitgated about 25% after 3 days. By 12/94, mitigated to nearly 100% Postauricular lesion was about 70% mitigated after 6 weeks. |
| 52/F | Mild psoriasis until age 30; severe psoriasis thereafter. | Topical and systemic corticosteroids; PUVA. | Right elbow: one 3 cm. lesion | 7 units at the site of the elbow lesion on 11/21/94. | Lesion in remission by 12/94. |
| 44/M | Psoriasis; eczema and pyriatis rosea. | Emollients, salicylic acid and tar shampoos. | One lesion on forehead (@ 1.5 cm.) | 10 units at site of lesion on 12/5/94. | Itching at site of lesion stopped within 3 days; scaling reduced within 5 days. |

TABLE 1-continued

| Age/Sex | Presenting Condition | Prior Treatment | Site of Lesion(s)/ Delivery | Dosage and Frequency of Injection | Post Injection Condition |
|---|---|---|---|---|---|
| | | | | | Lesion almost entirely mitigated within 2 weeks. |

The invention claimed is:

1. A method for mitigating or inducing remission of a skin lesion associated with a cutaneous cell-proliferative disorder in a mammal comprising administering a therapeutically effective amount of a Botulinum toxin in a pharmaceutically safe form to the mammal by delivery of the Botulinum toxin to the site of the lesion.

2. The method according to claim 1 wherein the Botulinum toxin is administered by subcutaneous injection.

3. The method according to claim 1 wherein the Botulinum toxin is Botulinum toxin A.

4. A method for controlling symptoms associated with the onset or presence of a cutaneous cell-proliferative disorder in a mammal comprising administering a therapeutically effective amount of a Botulinum toxin in a pharmaceutically safe form to the mammal by delivery of the Botulinum toxin to the mammal's skin.

5. A method for mitigating or inducing remission of a skin lesion associated with a cutaneous cell-proliferative disorder in a mammal comprising administering a therapeutically effective amount of a Tetanus toxin in a pharmaceutically safe form to the mammal by delivery of the Tetanus toxin to the site of the lesion.

6. The method according to claim 5 wherein the Tetanus toxin is administered by subcutaneous injection.

7. A method for mitigating or inducing remission of a skin lesion associated with a cutaneous cell-proliferative disorder in a mammal comprising administering a therapeutically effective amount of a biologically active fragment of a Tetanus toxin in a pharmaceutically safe form to the mammal by delivery of the Tetanus toxin to the site of the lesion.

8. The method according to claim 7 wherein the biologically active fragment is the lbc fragment of the Tetanus toxin.

9. A method for controlling symptoms associated with the onset or presence of a cutaneous cell-proliferative disorder in a mammal comprising administering a therapeutically effective amount of a Tetanus toxin in a pharmaceutically safe form to the mammal by delivery of the Tetanus toxin to the mammal's skin.

* * * * *